(12) United States Patent
Hudgins et al.

(10) Patent No.: US 8,007,519 B2
(45) Date of Patent: Aug. 30, 2011

(54) DYNAMIC SPINAL STABILIZATION SYSTEM AND METHOD OF USING THE SAME

(75) Inventors: R. Garryl Hudgins, Burnsville, MN (US); Thomas O. Viker, Arden Hills, MN (US); Guido Casutt, Rickenbach-Sulz (CH)

(73) Assignee: Zimmer Spine, Inc., Minneapolis, MN (US)

( * ) Notice: Subject to any disclaimer, the term of this patent is extended or adjusted under 35 U.S.C. 154(b) by 1151 days.

(21) Appl. No.: 11/685,329

(22) Filed: Mar. 13, 2007

(65) Prior Publication Data

US 2008/0234739 A1  Sep. 25, 2008

(51) Int. Cl.
*A61B 17/70* (2006.01)
(52) U.S. Cl. .......................... 606/255; 606/256; 606/257
(58) Field of Classification Search .................. 606/60, 606/246–279
See application file for complete search history.

(56) References Cited

U.S. PATENT DOCUMENTS

| | | | | |
|---|---|---|---|---|
| 4,998,936 A * | 3/1991 | Mehdian | ........................ | 606/250 |
| 5,108,397 A * | 4/1992 | White | .............................. | 606/60 |
| 5,415,661 A * | 5/1995 | Holmes | ......................... | 606/255 |
| 5,645,599 A | 7/1997 | Samani | | |
| 5,755,796 A * | 5/1998 | Ibo et al. | ..................... | 623/17.16 |
| 6,267,764 B1 * | 7/2001 | Elberg | ........................... | 606/255 |
| 6,743,231 B1 | 6/2004 | Gray et al. | | |
| 6,966,910 B2 * | 11/2005 | Ritland | ......................... | 606/257 |
| 7,727,259 B2 * | 6/2010 | Park | ............................... | 606/255 |
| 7,815,663 B2 * | 10/2010 | Trieu | ............................. | 606/254 |
| 2002/0035366 A1 | 3/2002 | Walder et al. | | |
| 2005/0113927 A1 * | 5/2005 | Malek | ........................ | 623/17.16 |
| 2006/0084982 A1 | 4/2006 | Kim | | |
| 2006/0111715 A1 | 5/2006 | Jackson | | |
| 2006/0229609 A1 * | 10/2006 | Wang | .............................. | 606/61 |
| 2006/0247637 A1 | 11/2006 | Colleran et al. | | |
| 2006/0282080 A1 * | 12/2006 | Albert et al. | ..................... | 606/61 |
| 2007/0016193 A1 * | 1/2007 | Ritland | ............................ | 606/61 |
| 2007/0173829 A1 * | 7/2007 | Drewry et al. | .................. | 606/61 |
| 2007/0288008 A1 * | 12/2007 | Park | .................................. | 606/61 |
| 2008/0103501 A1 * | 5/2008 | Ralph et al. | ..................... | 606/61 |

FOREIGN PATENT DOCUMENTS

| | | |
|---|---|---|
| EP | 0669109 | 8/1995 |
| FR | 2722980 | 7/1994 |
| NL | 7610576 | 3/1978 |
| WO | 9421185 | 9/1994 |
| WO | 2007002409 | 1/2007 |

* cited by examiner

*Primary Examiner* — Eduardo C Robert
*Assistant Examiner* — Jerry Cumberledge
(74) *Attorney, Agent, or Firm* — Seager, Tufte & Wickhem LLC

(57) ABSTRACT

A spinal stabilization system includes a pair of vertebral anchors and a flexible construct extending between the anchors to provide dynamic stabilization of the spine. The flexible construct includes first and second spring arms coupled to the anchors at first ends thereof and second ends coupled at a joint. The spring arms are capable of flexing toward and away from each other during movement of the spine. The system may include a biasing member for biasing movement of the spring arms toward and/or away from each other. The system may further include an adjustment feature that allows the distraction to be adjusted in situ. The stiffness characteristic of each of the spring arms may be selectively adjusted to meet the specific application. A method of stabilizing a spine includes securing anchors to selected vertebrae and coupling the flexible construct to the anchors through a top loading procedure. The flexible construct may be coupled so that a rotational axis of the flexible construct is anterior of a head portion of the anchors.

25 Claims, 6 Drawing Sheets

DYNAMIC SPINAL STABILIZATION SYSTEM AND METHOD OF USING THE SAME

FIELD OF THE INVENTION

The present invention generally relates to spinal support devices, and more particularly to an apparatus and method for dynamically stabilizing the spine.

BACKGROUND OF THE INVENTION

The spinal column is a highly complex system of bones and connective tissues that provides support for the body and protects the delicate spinal cord and nerves. The spinal column includes a series of vertebrae stacked one on top of the other, each vertebral body including an anterior portion of relatively weak cancellous bone and a posterior portion of relatively strong cortical bone. Situated between each vertebral body is an intervertebral disc that cushions and dampens compressive forces experienced by the spinal column. A vertebral canal containing the spinal cord and nerves is located behind the vertebral bodies. In spite of the complexities, the spine is a highly flexible structure, capable of a high degree of curvature and twist in nearly every direction. For example, the kinematics of the spine normally includes flexion, extension, rotation and lateral bending.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in the lumbar or cervical spine), and other disorders caused by abnormalities, disease, or trauma, such as ruptured or slipped discs, degenerative disc disease, fractured vertebra, and the like. Patients that suffer from such conditions usually experience extreme and debilitating pain, as well as diminished nerve function. These spinal disorders, pathologies, and injuries limit the spine's range of motion, or threaten the critical elements of the nervous system housed within the spinal column.

The treatment of acute and chronic spinal instabilities or deformities of the thoracic, lumbar, and sacral spine has traditionally involved rigid stabilization. For example, arthrodesis, or spine fusion, is one of the most common surgical interventions today. The purpose of fusion or rigid stabilization is the immobilization of a portion of the spine to affect treatment. Rigid stabilization typically includes implantation of a permanent, rigid assembly having metallic rods, plates and the like that secure selective vertebrae relative to each other. Spinal treatment using rigid stabilization, however, does have some disadvantages. For example, it has been shown that spine fusion decreases function by limiting the range of motion for patients in flexion, extension, rotation and lateral bending. Furthermore, it has been shown that spine fusion creates increased stresses and therefore, accelerated degeneration of adjacent non-fused segments. Another disadvantage of fusion is that it is an irreversible procedure.

More recently, dynamic stabilization has been used in spinal treatment procedures. Dynamic stabilization permits enhanced mobility of the spine while also providing sufficient stabilization to effect treatment. One example of a dynamic stabilization system is the Dynesys® system available from Zimmer Spine of Edina, Minn.

Dynamic stabilization systems are designed to more closely mimic natural spine movement, especially in flexion and extension. In many dynamic stabilization systems, however, the systems' rotational axis is positioned away from the normal rotational center of the spine in the posterior direction by a relatively large amount. Such posterior location of the stabilization system alters the natural movement of the spine. Thus, locating the stabilization system more anteriorly may provide an advantage.

Additionally, being able to easily adjust the stiffness characteristic of the system in a simple manner is also desired. Finally, providing a simple mechanism for adjustable distraction between vertebrae is another useful feature of a dynamic stabilization system.

Accordingly, there is a need for an improved dynamic stabilization system and method of using the same that addresses these objectives.

SUMMARY OF THE INVENTION

A dynamic stabilization system that provides many of these advantages includes a pair of vertebral anchors having a head portion and a bone attachment portion, and a flexible construct extending between the vertebral anchors for supporting the spine but yet allowing some mobility of the spine. The flexible construct includes first and second spring arms each having a first end coupled to one of the anchors and a second end that is coupled at a joint. The spring arms are capable of flexing toward and away from each other during movement of the spine, such as in flexion and extension.

In one embodiment, the joint is configured as a ball-and-socket joint that permits relative rotation between the first and second spring arms. The ball-and-socket joint also provides a self-aligning feature when spinal treatment calls for stabilization systems on both the right and left sides of the spine. In another embodiment, the joint may be configured as a hinge joint. In still another embodiment, the flexible construct may be a one-piece, unitary construction wherein the joint is configured as a bend portion in the flexible construct. The bend portion may be a single bend or alternately include multiple bend portions.

The stabilization system may include a biasing member for opposing movement of the spring arms away from and/or toward each other. In one embodiment, the biasing member may be configured as a resilient spring ring used when the joint is configured as a hinge. As the spring arms are moved toward or away from each other the spring ring gets compressed to generate a biasing force that opposes the motion. In another embodiment, the biasing member may be configured as a resilient cushion disposed between the spring arms. In this embodiment, the cushion is configured to prevent or reduce compressive overloading of the stabilization system. As such, the cushion imposes a biasing force on the spring arms as they are moved toward each other. In still another embodiment, however, the cushion may include a bridge member that imposes a biasing force as the spring arms are moved away from each other.

In another aspect of embodiments of the invention, the stabilization system may include an adjustment feature that allows the distraction of the system to be adjusted in situ. In one embodiment, the head portion of the anchors includes a connector having a tab extending therefrom with a plurality of teeth. The first end of the spring arms further include a slot also having a plurality of teeth disposed therein. The teeth on the tabs cooperate with the teeth in the slots to provide a one-way adjustment feature. In other words, the tabs are capable of moving relative to the slots in one direction but are prevented from moving relative to the slots in an opposite direction. In another embodiment, the tabs may include a slot having a multi-lobed configuration. The first ends of the spring arms may also have a corresponding multi-lobed configuration. The lobes cooperate to define a discrete number of distraction positions.

In still another aspect of the invention, the spring arms have stiffness characteristics that define, at least in part, the overall stiffness characteristic of the stabilization system. In one embodiment, the spring arms may have the same stiffness characteristic. In another embodiment, however, the stiffness characteristics of the first and second spring arms may be different. The stiffness characteristics may be adjusted by varying the length and/or thickness of a portion of the spring arms. Moreover, in cases where a stabilization system is coupled to both the right and left sides of the spine, the right stabilization system may have a stiffness characteristic different than the left stabilization system.

In further embodiments in accordance with the invention, the stabilization system may be incorporated within a larger spinal construct for treatment along an increased length of the spine. The spinal construct may, for example, include both dynamic stabilization portions and rigid stabilization portions, wherein the dynamic stabilization portions may be provided by embodiments of the stabilization systems described herein. To this end, the head portions of the anchors may include a connector that not only couples to the first ends of the flexible construct, but also include a channel or slot for receiving a rigid stabilization rod. This allows the relatively larger spinal construct with modularity with rigid stabilization portions capable of being positioned adjacent the dynamic portions provided by embodiments of the invention.

A method of stabilizing a spine includes securing at least a first and second anchor to respective first and second vertebrae and then coupling a flexible construct to the anchors. The flexible construct may be coupled to the anchors using a top loading procedure that essentially permits assembly of the stabilization system by coupling from the posterior side. This may be accomplished, for example, by coupling the connectors to the flexible construct and then coupling the connectors to the anchors by a snap-fit feature. Moreover, the flexible construct may be coupled to the anchors so that the rotational axis of the flexible construct is anterior of the head portion of the anchors.

In one embodiment, the anchors may be configured as polyaxial screws having a head portion adapted to be coupled to the flexible construct and a threaded portion adapted to be coupled to bone and having one end coupled to the head portion and the other end defining a tip. The threaded portion includes a tapered core or shaft that decreases in diameter in a direction from the head portion toward the tip. A helical thread is disposed on the shaft and has a height that decreases in a direction from the tip toward the head portion. The thread also defines a land that increases in a direction from the tip toward the head portion.

These and other objects, advantages and features of the invention will become more readily apparent to those of ordinary skill in the art upon review of the following detailed description taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
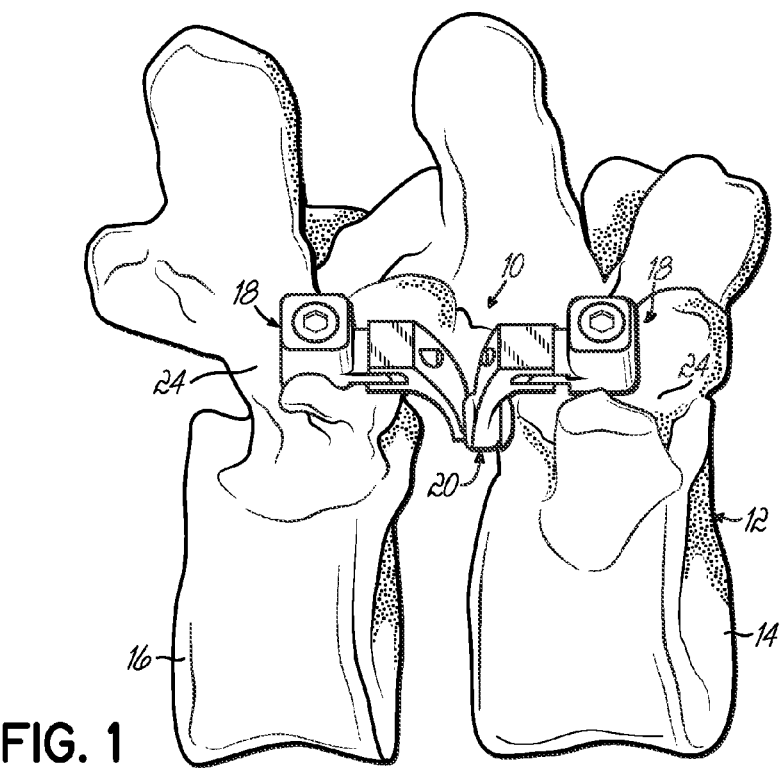
FIG. 1 is a perspective view of an exemplary stabilization system in accordance with an embodiment of the invention implanted on the spine.

Referring now to the figures, and to FIG. 1 in particular, a spinal stabilization system 10 is shown implanted into a segment of the spine 12 defined by serially positioned spinal elements in the form of adjacent vertebrae 14, 16 separated by a disc (not shown). The stabilization system 10 includes a pair of anchors 18 installed in vertebrae 14, 16 and a flexible construct 20 coupled to and extending between the two anchors 18 to control abnormal motion of the spine 12, while otherwise leaving the spinal segment mobile. In the exemplary embodiment, as well as the other spinal stabilization system embodiments, the flexible construct 20 is configured to more closely align with the natural center of rotation of the spine 12 and can be positioned more anterior relative to the pedicles 24 of the vertebrae 14, 16 to which the anchors 18 are secured.

Figure 2:
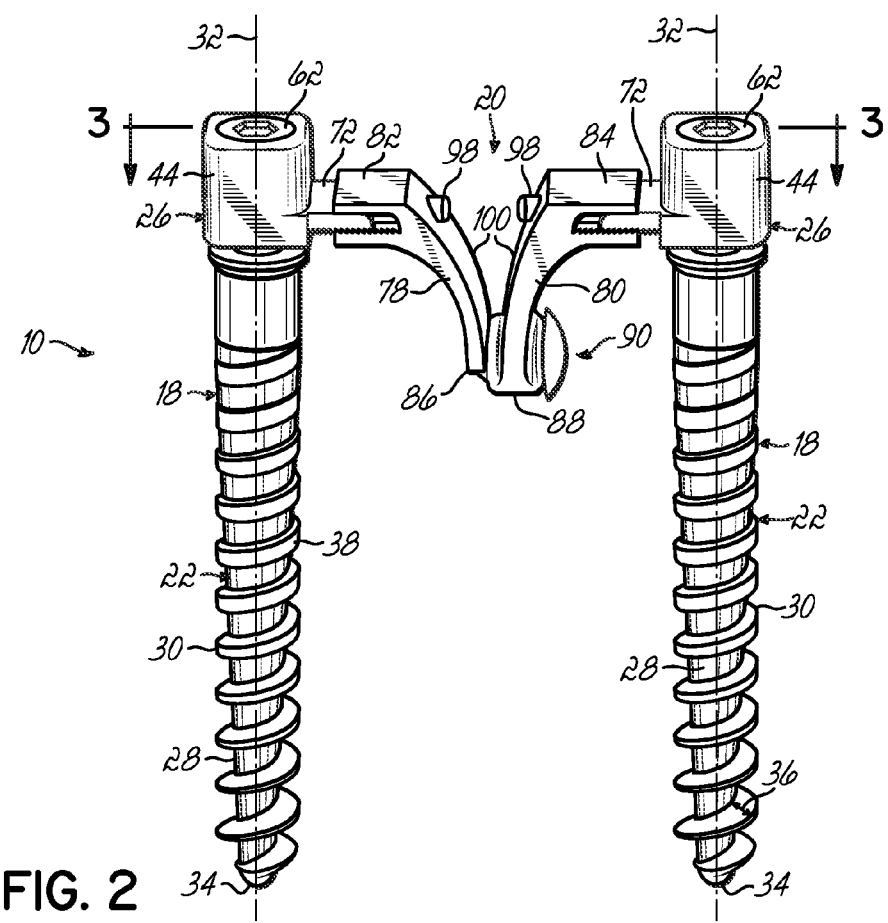
FIG. 2 is a perspective view of the stabilization system shown in FIG. 1.

FIG. 2 illustrates an exemplary embodiment of the spinal stabilization system 10 in more detail. As shown in this figure, each anchor 18 may be configured as a polyaxial pedicle screw having a threaded portion 22 adapted to facilitate coupling between the anchor 18 and the pedicles 24 (FIG. 1) of the vertebrae 14, 16, and a head portion 26 adapted to couple to the flexible construct 20. As shown in FIG. 1, the spinal stabilization system 10 is configured to move the rotational axis of the system anteriorly. In the exemplary embodiment, the flexible construct 20 is coupled to the anchors 18 so that the rotational axis of the flexible construct 20 is positioned anterior to head portion 26 of the anchors 18. While pedicle screws are shown and described herein, those of ordinary skill in the art will appreciate that the spinal anchors 18 may take the form of hooks or other devices coupled to the spine.

The threaded portion 22 of anchor 18 includes a tapered core 28 and a helically wound thread 30 projecting outwardly therefrom and extending along a longitudinal axis 32 of the anchor 18 from a tip 34 toward the head portion 26. The thread 30 is configured to have a height 36 that progressively decreases in a direction from the tip 34 toward the head portion 26. The thread 30 is further configured so that the crest of the thread 30 defines a land 38 that progressively increases in a direction from the tip 34 toward the head portion 26. Thus, the thread is initially sharp adjacent the tip 34 and becomes progressively flatter or blunter in a direction toward the head portion 26. The tapered core 28 and the configurations of thread 30 may promote radial spongiosa compression. Moreover, the anchors 18 may include a hydroxyapatite (HA) coating for long-term stability by promoting accelerated bone on-growth during the early postoperative period for an enhanced screw-bone interface. The anchors 18 may be inserted into the pedicles 24 of vertebrae 14, 16 using techniques generally known in the art.

Figure 3:
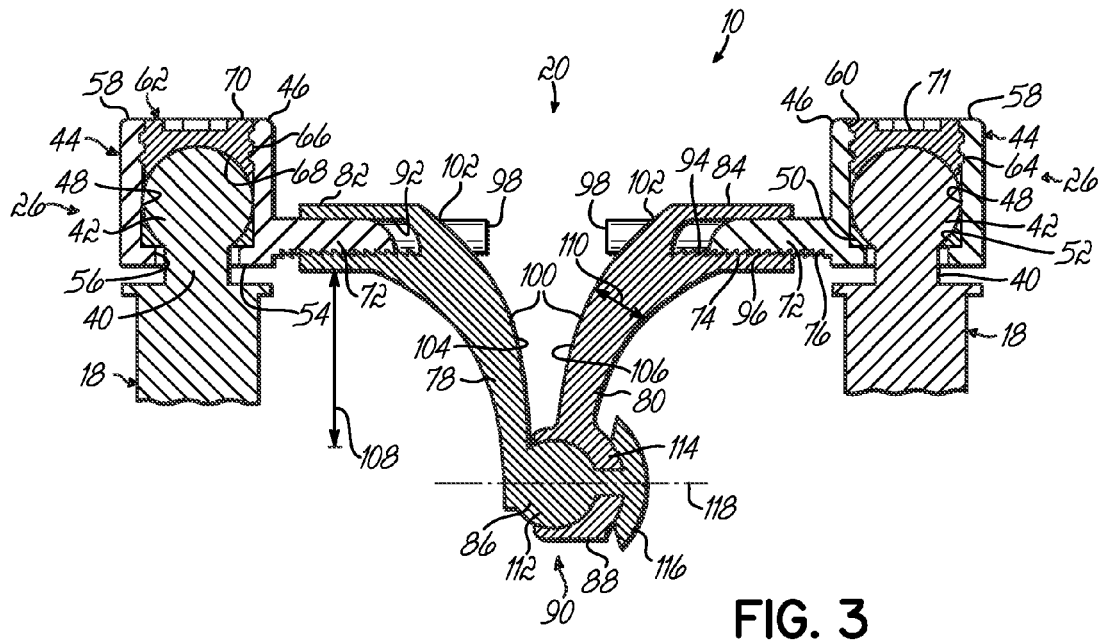
FIG. 3 is a partial cross-sectional view of the stabilization system shown in FIG. 2.

As best illustrated in FIG. 3, the head portion 26 of the anchors 18 includes a stem 40 projecting from threaded portion 22 and having a cross dimension (e.g., diameter) smaller than a cross dimension of the threaded portion 22 adjacent the stem 40 to define a narrowed portion, or neck, of the anchor 18. A generally spherical ball portion 42, having a cross dimension larger than the stem 40, is coupled to the stem 40 at an end opposite the threaded portion 22. The head portion 26 further includes a connector 44 removably coupled to the anchor 18 at the ball/stem portion of the anchor 18. For instance, the connector 44 may be removably coupled to the ball/stem portion of the anchor 18 via a snap-fit feature. The ability to selectively remove the connectors 44 from the threaded portion 22 allows the flexible construct 20 to be removed from the stabilization system 10 without also removing the anchors 18 from the pedicles 24. This aspect allows the stabilization system 10 to be appropriately adjusted in a quick and convenient manner while also avoiding the problems associated with excessive engagement/disengagement of the anchors 18 with the pedicles 24.

The connector 44 includes a generally rectangular body 46 defining an interior cavity 48 adapted to receive the ball portion 42 projecting from threaded portion 22. A retaining ring 50 may be positioned in a lower end of the cavity 48 and includes an inner surface 52 having a shape corresponding to the shape of ball portion 42. Although the connector body 46 is shown and described herein as generally rectangular, the invention is not so limited as those of ordinary skill in the art will recognize that the connector 44 may have a wide variety of shapes. Moreover, those of ordinary skill in the art will recognize that while ball portion 42 is shown and described as spherical, other shapes providing an enlarged portion relative to stem 40 are within the scope of the invention.

A lower surface 54 of connector body 46 includes a bore 56 open to interior cavity 48. The bore 56 is adapted to receive stem 40 therein when the connector 44 is coupled to threaded portion 22 via ball portion 42 (FIG. 3). The bore 56 has a cross dimension larger than the cross dimension of the stem 40 so as to allow the connector 44 to move about ball portion 42 in essentially an infinite number of alignments (i.e., the anchor 18 is polyaxial). The polyaxial feature of anchors 18 facilitates use of the stabilization system 10 and allows a surgeon to accurately position the system on the spine 12.

An upper surface 58 of connector body 46 also includes a bore 60 open to interior cavity 48. The bore 60 is adapted to receive a setscrew 62 therein to securely couple the connector 44 to the threaded portion 22 of anchor 18. To this end, the bore 60 includes a set of internal threads 64 that cooperate with a set of external threads 66 on setscrew 62 to couple the setscrew 62 to the connector body 46. A lower surface 68 of the setscrew 62 is generally arcuately shaped to correspond to the shape of the ball portion 42. The corresponding shape between the ball portion 42 and the setscrew 62 facilitates the securing of the connector 44 to the threaded portion 22 in the infinite number of alignments. An upper surface 70 of setscrew 62 includes a bore 71, such as a countersunk hexagonal bore, adapted to engage a tool (not shown) for rotating the setscrew 62. As the setscrew 62 is tightened, the ball portion 42 is clamped between the arcuately shaped lower surface 68 of setscrew 62 and the inner surface 52 of retaining ring 50 to secure the connector 44 to the threaded portion 22 of anchor 18.

As shown in FIGS. 1-3, each connector 44 of anchors 18 includes a plate-like tab 72 extending therefrom and projecting toward the opposed anchor 18, i.e., the tabs 72 project toward each other. Each of the tabs 72 adjustably couple to the flexible construct 20. Additionally, each of the tabs 72 includes a lower surface 74 including a plurality of serrations or teeth 76. The upper surface may also include a plurality of teeth, or alternately, present a smooth surface as shown in FIG. 3. As explained in more detail below, the teeth 76 promote coupling between the connectors 44 and the flexible construct 20. Those of ordinary skill in the art will recognize that tabs 72 may include other coupling-promoting structures other than, or in addition to, the teeth 76 to promote coupling between the connectors 44 and the flexible construct 20. The invention is therefore not limited to the teeth 76 shown and described herein.

Again referring to FIGS. 1-3, the flexible construct 20 includes a pair of spring arms 78, 80 having respective first ends 82, 84 coupled to a tab 72 of a corresponding anchor 18, and respective second ends 86, 88 coupled to each other at a joint 90 such that flexible construct 20 has a generally V-shaped configuration. The first ends 82, 84 of the spring arms 78, 80 have a similar construction and include a generally U-shaped slot 92 that receives a corresponding tab 72 therein. A lower surface 94 of each slot 92 includes a plurality of teeth 96 that cooperate with the teeth 76 on corresponding tabs 72 to facilitate an adjustable connection between connectors 44 and spring arms 78, 80. The upper surface of slots 92 may also include a plurality of teeth, or present a smooth surface as shown in FIG. 3.

The connection between the first ends 82, 84 of spring arms 78, 80 and the tabs 72 of anchors 18 provide convenient adjustability in distraction between the adjacent vertebrae 14,16. For example, adjustment in distraction of the vertebrae 14, 16 may be performed in situ, therefore eliminating the need to remove the entire stabilization system 10, or at least a portion thereof from the surgical site in the patient. To this end, the teeth 76 on the tabs 72 and the teeth 96 on the spring arms 78, 80 cooperate to provide a one-way adjustment feature. In particular, each of the teeth 76, 96 are configured to have a first low-slope surface relative to a generally planar surface that defines the lower surfaces 74, 94 of the tabs 72 and slots 92, respectively, adjacent a high-slope surface (e.g., a surface perpendicular to the generally planar surface).

The low-slope and high-slope surfaces are configured such that the first ends 82, 84 of the spring arms 78, 80 are capable of moving away from the tabs 72 (via the low-slope surfaces), but are prevented from moving toward the tabs 72 (via the high-slope surfaces). Accordingly, once the vertebrae 14, 16 are distracted to their desired location, such as by devices generally known in the art, the stabilization system 10 may be coupled to the spine 12 and adjusted in situ so as to effectuate the desired amount of distraction. For example, the stabilization system 10 may initially be configured such that the tabs 72 are fully inserted into slots 92 and the desired amount of distraction between the vertebrae 14,16 accommodated by moving the tabs 72 and first ends 82, 84 of the spring arms 78, 80 in opposite directions, i.e., the direction permitted by the one-way adjustment feature, until the connectors 44 may be coupled to the ball portions 42 of the anchors 18. The ability to adjust the stabilization system 10 without removing the stabilization system 10 from the spine 12, provides advantages over current systems and facilitates the use of the system 10 during spinal surgical procedures.

As shown in FIGS. 2 and 3, each of the tabs 72 include a securing pin 98 extending from an end of the tabs 72 and away from their respective connectors 44. The securing pins 98 may be integrally formed with the tabs 72, or alternately, be coupled thereto by suitable means, such as via a threaded connection, adhesives, sonic welding, etc. An inner surface 100 on each of the spring arms 78, 80 adjacent first ends 82, 84 include a bore 102 open to slot 92 and receive the securing pin 98 therein during manufacturing or assembly. The securing pins 98 prevent relative movement between the spring arms 78, 80 and tabs 72 in a lateral direction, i.e., in a direction generally parallel to the low and high-slope surfaces of the teeth 76, 96. Accordingly, the spring arms 78, 80 are prevented from essentially slipping off the side edges of the tabs 72 during installation and use of the stabilization system 10.

In an exemplary embodiment, the spring arms 78, 80 may have a metallic construction but are so constructed so as to be capable of flexing. The metallic construction minimizes material conditioning and creep, thus maintaining the initial distraction of the vertebrae 14, 16, but yet allows dynamic stabilization of the spine 12 to be realized. For example, the spring arms 78, 80 are capable of flexing toward and away from each other during flexion and extension of the spine 12. In particular, an intermediate portion 104, 106 of spring arms 78, 80 may be configured to provide a desired amount of flexion and extension of the spine 12, depending on the particular application. For instance, the intermediate portions 104, 106 have a length 108 and a thickness 110 that may be manipulated to provide a desired amount of flexion and extension of the spine 12. In essence, by manipulating the configuration of the intermediate portions 104, 106, such as through the length 108 and thickness 110, the overall stiffness of the stabilization system 10 may be adjusted according to the specific application. Those of ordinary skill in the art will recognize other approaches to varying the stiffness of the spring arms. For example and without limitation, the material of the spring arm may be manipulated to achieve a desired stiffness.

In one embodiment, the spring arms 78, 80 may have the same configuration or design such that the stiffness characteristic of each spring arm 78, 80 is substantially the same. In another embodiment, however, the stiffness characteristics of the spring arms 78, 80 may be different. Thus, depending on the specific application, spring arm 78 may be stiffer than spring arm 80, or vice versa. This may be accomplished, for example, by making one spring arm thicker than the other spring arm. In addition, spring arm 78 may be shorter or longer than spring arm 80. Spring arms having different lengths may enhance treatment of certain spinal diseases, such as spondylolisthesis. In addition, in spinal treatments that call for a stabilization system 10 on both sides of the spine 12 (not shown), the stiffness characteristic of the right stabilization system may be different than the stiffness characteristic of the left stabilization system, depending on the specific application. Again, such a configuration may be beneficial in the treatment of certain spinal diseases.

As noted above, the second ends 86, 88 of spring arms 78, 80 are coupled together at a joint 90. The joint 90 may be configured in a manner depending on the specific application. For example, as best shown in FIG. 3, joint 90 may be configured as a ball-and-socket joint. To this end, the second end 86 of spring arm 78 includes a ball portion 112 and the second end 88 of spring arm 80 includes a socket or cavity portion 114 that receives ball portion 112 therein. The ball 112 may include a generally T-shaped stem 116 for coupling ends 86, 88 together. In one aspect of the invention, the ball-and-socket joint may provide additional degrees of motion to the stabilization system 10. Movement of the spring arms 78, 80 toward and away from each other along, for example, the axis of spine 12 is permitted due to the resiliency or flexibility of the spring arms 78, 80, as generally described above. In addition, however, the ball-and-socket joint may also allow relative rotation of the spring arms 78, 80 about an axis 118 that is generally parallel to the axis of spine 12. The ability of the spring arms 78, 80 to rotate about axis 118 may be advantageous in the treatment of certain spinal diseases. For example, the ball-and-socket joint may be advantageous for the treatment of scoliosis to accommodate the abnormal lateral curvature of the spine 12.

Figure 4:
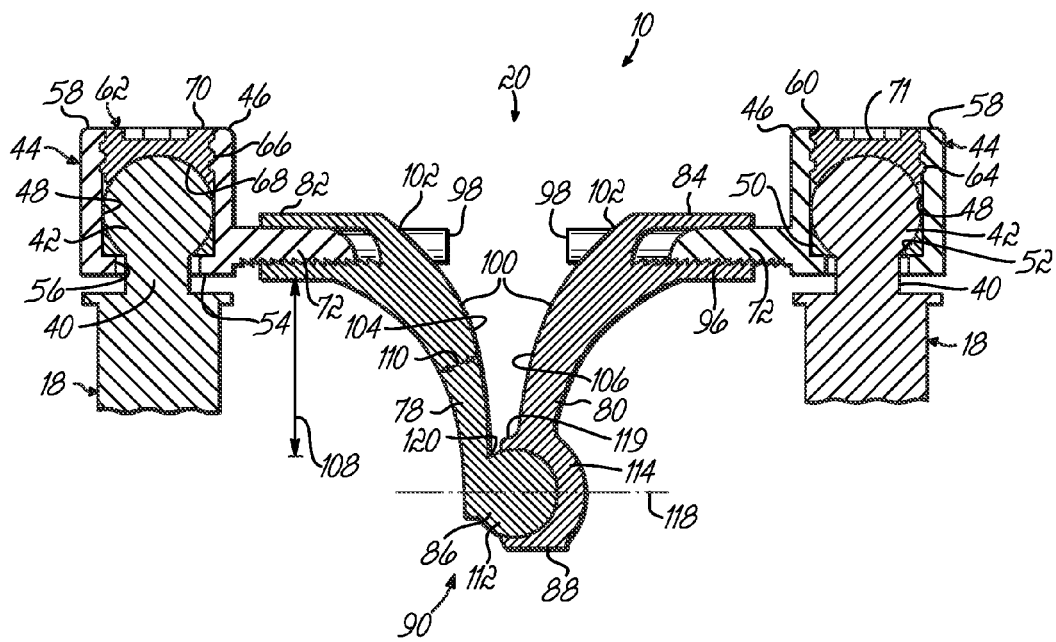
FIG. 4 is a partial cross-sectional view of a stabilization system in accordance with an alternate embodiment of the invention.

FIG. 4, in which like reference numerals refer to like features in FIGS. 1-3, illustrates an alternate ball-and-socket joint similar to that shown in FIGS. 1-3. The joint 90 in FIG. 4 permits relative rotation of the spring arms 78, 80 about axis 118. In addition to this, however, joint 90 may also provide some relatively small range of free movement of the spring arms 78, 80 toward and away from each other before movement toward and away from each other is biased by the resiliency of the spring arms 78, 80. To this end, the socket portion 114 may have an outer edge 119 that is spaced from the junction 120 between the ball portion 112 and the spring arm 80. This spacing allows the spring arms 78, 80 to freely move toward or away from each other prior to the outer edge 119 of the socket portion 114 contacting the junction 120. Once the outer edge 119 contacts function 120, any further movement of the spring arms 78, 80 toward or away from each other is biased by the resiliency of the arms 78, 80.

The ball-and-socket constructions shown in FIGS. 3 and 4 are generally alignment forgiving and will essentially self-align during installation of the stabilization system 10. This may be especially important when stabilization systems are being located on both the right and left sides of the spine 12. For instance, in these cases, alignment of the rotational axis of the spring arms 78, 80 at joint 90 on each side of the spine 12 is desirable, but may be difficult to achieve during a surgical procedure. The ball-and-socket configuration does not depend of a single rotational axis and therefore provides some robustness to alignment of the right and left stabilization systems. In addition, the ball-and-socket joint 90 may be beneficial in the treatment of certain diseases, such as scoliosis even when it is not possible to distract the vertebrae to the same level on both sides.

Figure 5:
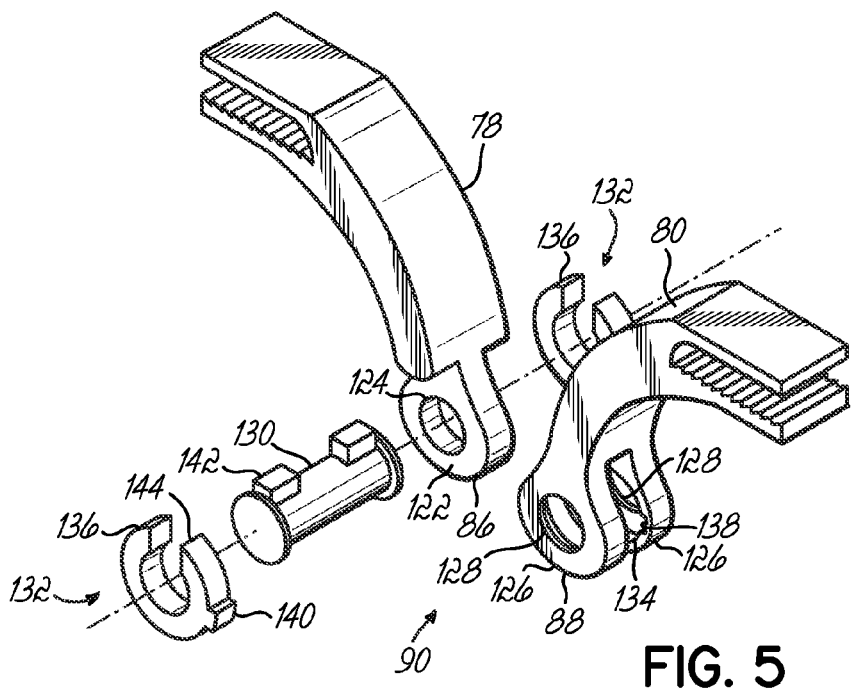
FIG. 5 is a partial disassembled perspective view of a stabilization system in accordance with an alternate embodiment of the invention.

Although the joint 90 is shown and described in FIGS. 3 and 4 as a ball-and-socket joint, the joint 90 may have other configurations in accordance with embodiments of the invention. For example, and as shown in FIG. 5, in which like reference numerals refer to like features in FIGS. 1-3, the joint 90 may be configured as a spring-biased hinge. To this end, the second end 86 of spring arm 78 may include an extending lobe 122 having an aperture 124 therein and the second end 88 of spring arm 80 may include a pair of spaced apart lobes 126 each also having an aperture 128 therein. The lobe 122 on spring arm 78 fits between the lobes 126 on spring arm 80 so that the apertures 124, 128 align with each other. A pin member 130 is inserted through the apertures 124, 128 to secure the spring arms 78, 80 together and effectuate the hinged connection. In one embodiment, the pin member 130 is securely coupled to spring arm 78 so that pin member 130 rotates with movement of spring arm 78, and spring arm 80 is capable of rotation about the pin member 130, for reasons described below. While spring arm 78 is described as having one lobe and spring arm 80 has the pair of spaced apart lobes, those of ordinary skill in the art will recognize that spring arm 78 may have the pair of spaced apart lobes and spring arm 80 may have only one lobe. Those of ordinary skill in the art will further recognize that additional lobes may be included at the hinge joint and be within the scope of the invention.

The joint 90 shown in FIG. 5 further includes a biasing member 132 that essentially operates as a rotational damper to oppose movement of the spring arms 78, 80 toward and away from each other. To this end, at least one of the apertures 128 in lobes 126, and preferably both of the apertures 128, include an enlarged bore 134 disposed on an inner surface of the lobes 126 that receive a resilient spring ring 136 therein. The spring ring 136 is capable of being compressed and may be formed from a variety of materials, such as suitable polymeric materials including polycarbonate urethane, or other elastomeric materials capable of being compressed. As shown in FIG. 5, the bore 134 includes a recess 138 that receives a projection or detent 140 projecting outwardly from the spring ring 136. When the detent 140 is positioned within the recess 138, the spring ring 136 is prevented from rotating relative to the bore 134. Furthermore, the pin member 130 includes a detent or tab 142 that is received within a notch or cutout 144 in the spring ring 136.

In operation, the spring arms 78, 80 have an unbiased separation distance for which the tab 142 is positioned in notch 144 and the spring ring 136 is not deformed. During flexion or extension of the spine 12, wherein the spring arms 78, 80 are moved toward or away from each other, the tab 142 rotates relative to the bore 134 causing the tab 142 to contact a wall of the notch 144. Because the spring ring 136 is prevented from moving relative to the bore 134, the spring ring 136 is compressed along a generally circumferential direction. As the spring ring 136 is compressed, it generates a biasing force that resists the movement of the spring arms 78, 80 toward or away from each other. The magnitude of the biasing force typically increases with increased compression of the spring ring 136.

Thus, in this embodiment, the stiffness characteristics of the stabilizing system 10 may be due to the flexibility of the spring arms 78, 80 themselves, as generally described above; due to the damping caused by the resilient spring ring 136 without substantial flexing of the spring arms 78, 80; or due to the combination of the flexing of the spring arms 78, 80 and the damping caused by the spring ring 136. Moreover, those of ordinary skill in the art will recognize that the spring arm 78 may include the multiple lobes and include the biasing member and rotate about pin member 130 while spring arm 80 is securely coupled to pin member 130 so as to rotate therewith. Additionally, other biasing members, such as coil springs or other compressible elements, may be used with the invention. The invention, therefore, is not limited to the specific configuration of the hinged joint and biasing member shown and described herein.

Figure 6:
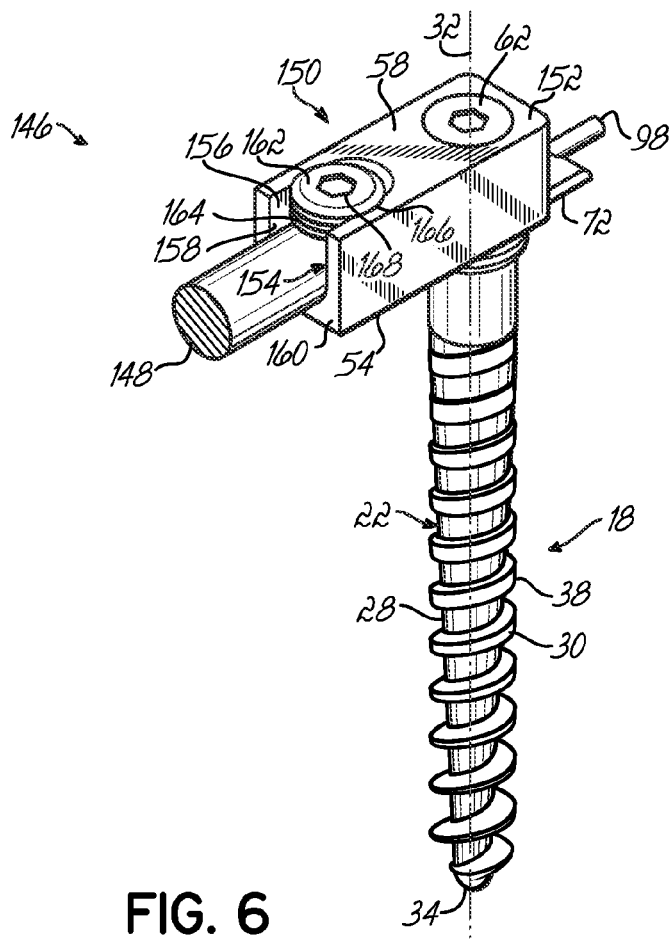
FIG. 6 is a partial perspective view of a stabilization system in accordance with an alternate embodiment of the invention incorporated into a spinal device.
Figure 7:
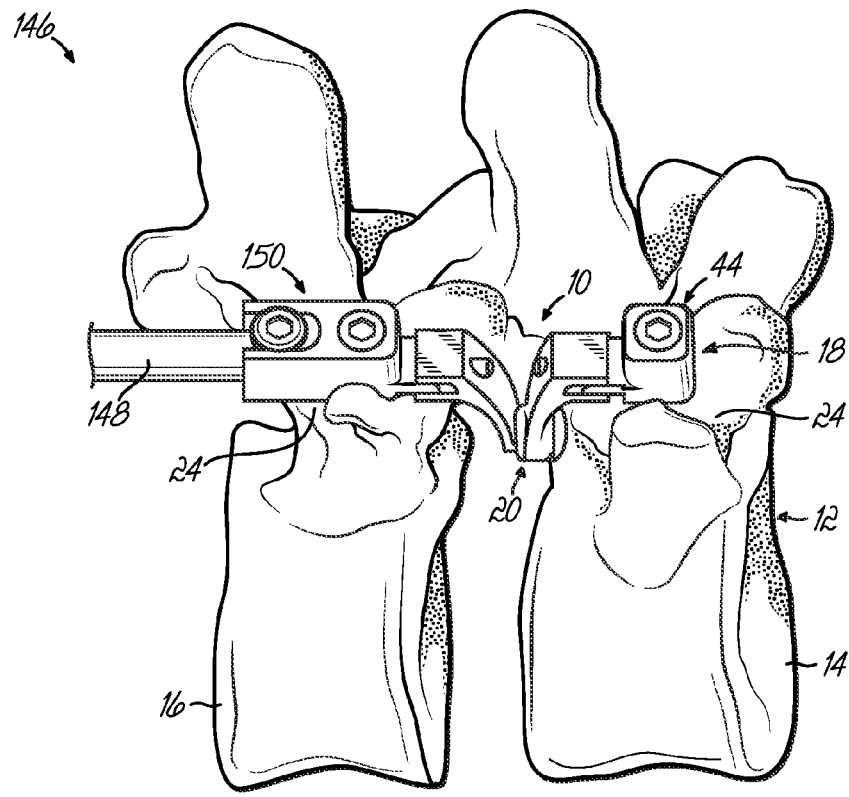
FIG. 7 is a perspective view of the spinal device shown in FIG. 6 implanted on the spine.

In reference to FIGS. 6 and 7, the stabilization system 10 may be incorporated into a larger spinal device 146 for treating various spinal conditions that span multiple vertebrae. Such a spinal device 146 may, for example, include selective portions with dynamic stabilization, corresponding to the position(s) of stabilization system 10, and other selective portion(s) with rigid stabilization, corresponding to rigid constructs, such as rigid stabilization rods 148. To this end, the stabilization system 10 may include a connector 150 similar to connectors 44 as shown and described above. Connector 150 is similar to connector 44 and only the modifications will be discussed in detail.

The connector 150 includes an enlarged body 152 as compared to body 46 of connector 44. Body 152 includes interior cavity 48 for receiving ball portion 42 of anchor 18, lower surface 54, bore 56, upper surface 58, bore 60, and setscrew 62 as previously described. Body 152 further includes a channel 154 formed therein that defines openings 156, 158 in upper surface 58 and side surface 160. The channel 154 receives an end of stabilization rod 148. The bottom surface of channel 154 may be arcuately shaped to generally correspond to the shape of the stabilization rod 148. A setscrew 162 may be used to retain the stabilization rod 148 with the connector 150. To this end, setscrew 162 may include external threads 164 that engage a corresponding set of internal threads (not shown) formed in a bore 166 that communicates with channel 154. Bore 166 is open to upper surface 58 and is generally perpendicular to the channel 154. Setscrew 162 may include a bore 168, such as a countersunk hexagonal bore, for engagement by a tool (not shown) for rotating setscrew 162. In use, the end of the stabilization rod 148 may be inserted into channel 154. A tool may then be used to rotate setscrew 162 so that a bottom surface of the setscrew 162 engages the rod 148. The setscrew 162 is further rotated such that the rod 148 is securely clamped between the bottom surface of the channel 154 and the bottom surface of the setscrew 162. The rod 148 is then secured from movement relative to connector 150.

FIG. 7 illustrates connector 150 as it might be used to form a spinal device 146 that effectuates spinal treatment over several vertebrae levels. Although FIG. 7 shows one of the anchors 18 having connector 150 and the other configured as connector 44, the invention is not so limited. Those of ordinary skill in the art will appreciate that both connectors used in spinal device 146 may be configured as connector 150 so that stabilization rods 148 may extend from both ends of stabilization system 10 (not shown). Alternately, the left connector, as shown in FIG. 7, may be configured as connector 44, and the right connector, as shown in FIG. 7, may be configured as connector 150 so that the stabilization rod 148 extends from the other end of stabilization system 10 (not shown). Those of ordinary skill in the art will recognize that relatively large and complex spinal devices 146 may be construed using multiple rigid and dynamic stabilization portions.

Figure 8:
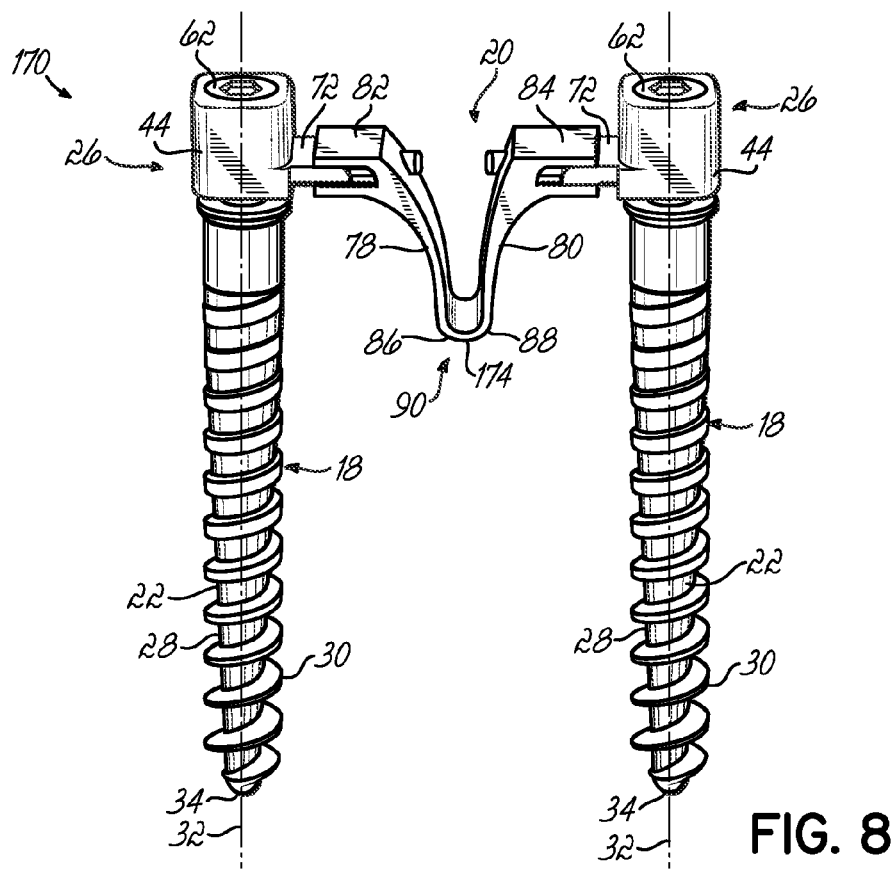
FIG. 8 is a perspective view of a stabilization system in accordance with an alternate embodiment of the invention.

FIG. 8, in which like reference numerals refer to like features in FIGS. 1-3, illustrates a stabilization system 170 in accordance with an alternate embodiment of the invention. The stabilization system 170 is similar to stabilization system 10 and only the differences will be discussed in detail. As shown in this figure, the flexible construct 20, including spring arms 78, 80 and joint 90, has a unitary, one-piece design. As such, the joint 90 may be formed as a bend or loop portion 174 similar to a living hinge. The flexibility of the spring arms 78, 80 as well as any additional flexibility due to the bend portion 174 provides the stiffness characteristic of stabilization system 170. The stiffness characteristic of stabilization system 170 may be adjusted by varying the length and thickness of the intermediate portions of the spring arms 78, 80 in a manner similar to that described above. Alternately, the joint 90 may be configured with more than one bend portion 174 connecting the spring arms 78, 80 (not shown) so as to achieve a desired stiffness characteristic for the system 170. The stabilization system 170 operates in a manner similar to that described above. Moreover, stabilization system 170 may be incorporated within a larger spinal device with the use of connector 150 as described above.

Figure 9:
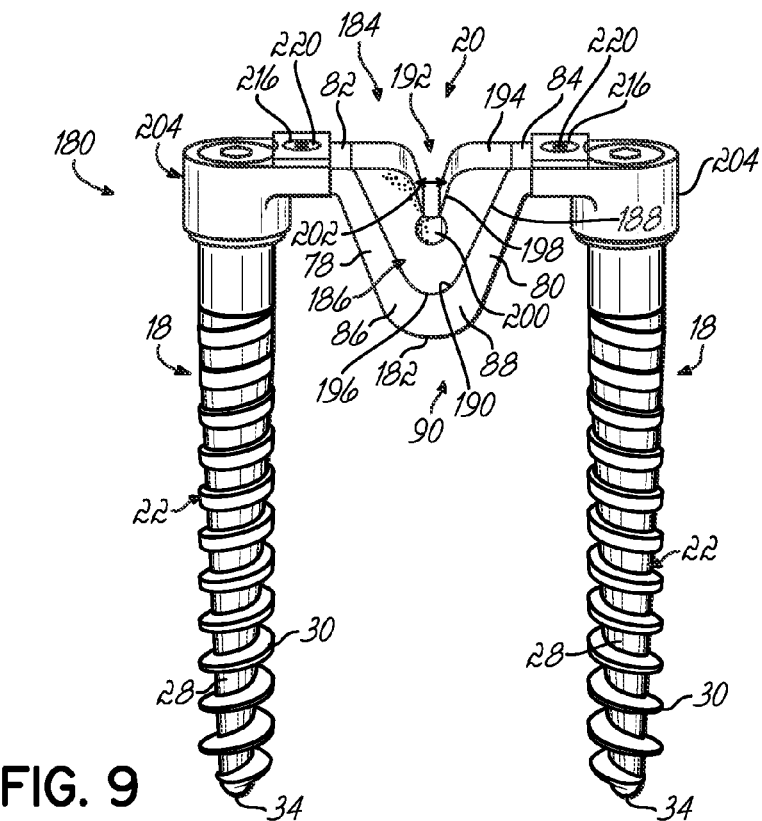
FIG. 9 is a perspective view of a stabilization system in accordance with an alternate embodiment of the invention.
Figure 10:
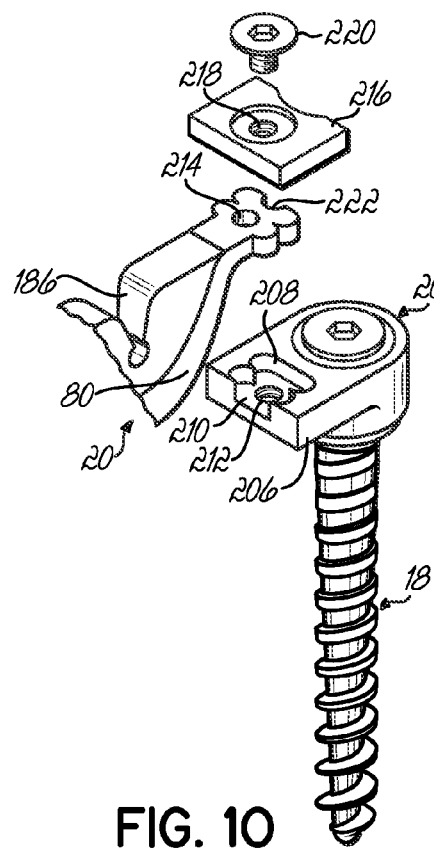
FIG. 10 is a partial perspective view of the stabilization system shown in FIG. 9.

FIGS. 9 and 10, in which like reference numerals refer to like features in FIGS. 1-3, illustrate a stabilization system 180 in accordance with another embodiment of the invention. The stabilization system 180 includes a pair of anchors 18 similar to that described above. In this embodiment, the flexible construct 20 includes spring arms 78, 80 having first ends 82, 84 coupled to the anchors, as described in more detail below, and second ends 86, 88 coupled at joint 90. Joint 90 is configured similar to that shown in FIG. 8 and thus includes a bend portion 182 that gives the flexible construct 20 a generally V-shaped configuration.

In this embodiment, stabilization system 180 may be configured to reduce compressive overloading of the flexible construct 20 during, for example, extension of the spine 20. To this end, stabilization system 180 may include a biasing member that essentially operates as a damper disposed between the spring arms 78, 80 to oppose movement of the spring arms 78, 80 toward each other. The biasing member may be configured as a generally V-shaped cushion 186 having an outer surface 188 coupled to an inner surface 190 of the spring arms 78, 80 and joint 90. Cushion 186 includes a slot or cutout portion 192 centrally disposed therein that extends from an upper surface 194 of the cushion 186 toward the apex 196. The cutout portion 192 includes an angled portion 198 that converges in a direction from the upper surface 194 toward the apex 196 and terminates in a generally circular portion 200. The angled portion 198 defines opposed surfaces that are spaced from each other to define a gap 202 therebetween.

In operation, as the spring arms 78, 80 move toward one another, such as during extension of the spine 12, only the resiliency of the spring arms 78, 80 biases the initial movement toward each other. In other words, due to the gap 202 between the angled surfaces in the cutout portion 192, the cushion 186 does not impose a force to bias the initial movement of the spring arms 78, 80 toward one another. After a predetermined amount of movement of the spring arms 78, 80 toward each other, i.e., the gap 202 may be pre-selected depending on the specific application, the surfaces along angled portion 198 contact each other. At this point, any further movement of the spring arms 78, 80 toward each other compresses the cushion 186, which generates a biasing force that opposes such motion of the spring arms 78, 80. The magnitude of the biasing force typically increases with increased compression of the cushion 186. In this way, the cushion 186 prevents or reduces the risk of damaging the stabilization system 180 due to compressive overloading.

The cushion 186 may be coupled to the flexible construct 20 during a separate assembly process, such as through an adhesive process. Alternately, the cushion 186 may be integrally formed with the flexible construct 20 during manufacturing, such as through a molding and/or an over molding process, as is generally known in the art. The cushion 186 may also be formed from a variety of materials, such as suitable polymeric materials including polycarbonate urethane, or other elastomeric materials capable of being compressed. The flexible construct 20 may be a unitary, one-piece construction formed from metal or suitable polymers known to those of ordinary skill in the art. For example, in one embodiment, the flexible construct 20 may be formed from fiber-reinforced polyetheretherketone (PEEK). In another embodiment, nitinol may be used as the material for all or part of the flexible construct 20. In other embodiments, the flexible construct 20 may be a composite member composed of two or more materials.

As shown in FIG. 10, the connection between the flexible construct 20 and the anchors 18 may have a different configuration to that shown in FIGS. 1-3. As shown in this figure, the anchors 18 include connectors 204 having a plate-like tab 206 extending therefrom and projecting toward the opposed anchor 18, i.e., the tabs 206 project toward each other. Each tab 206 includes a channel or slot 208 formed therein having a multi-lobed configuration that receives a first end of one of the spring arms 78, 80. The slot 208 includes a bottom surface 210 that includes a threaded aperture 212, the purpose of which is described below.

As also shown in FIG. 10, the first ends 82, 84 of spring arms 78, 80 also have a multi-lobed configuration that correspond to the shape of the slot 208 in tabs 206 of connectors 204. The first ends 82, 84 also include an aperture 214 there through for securing the first ends 82, 84 to connectors 204, as discussed in more detail below. The lobes on the first ends 82, 84 (two shown) cooperate with the lobes in slot 208 (also two shown) to define a plurality of discrete distraction positions between vertebrae. For example, the configuration shown in FIG. 10 includes three possible distraction positions. In one distraction position, each of the lobes on the first ends 82, 84 is located within a lobe in slots 208, i.e., the first ends are fully inserted within slots 208 on both the anchors 18. In another position, one of the ends has its outer most lobe positioned within the outer most lobe in slot 208 while the other end is fully inserted within the other slot 208. In the last position, both ends are configured so that its outer most lobe is positioned within the outer most lobe in slot 208. This configuration would provide the greatest amount of distraction between vertebrae. While the first ends 82, 84 and slots 208 are shown as having two lobes, additional lobes may be included so as to increase the number of distraction positions associated with the stabilization device 180.

To secure the first ends 82, 84 to the respective connectors 204, stabilization system 180 may include a plate-like cap 216 having an aperture 218 therein for receiving a threaded fastener 220. When the first ends 82, 84 are fully inserted within the slots 208, the cap 216 may be placed on the upper surface of the connector 204 so that the aperture 218 in the cap 216 aligns with the aperture 214 in the first ends 82, 84 and aligns with the threaded aperture 212 in the bottom surfaces 210 of slots 208. The threaded fastener 220 may be inserted through the apertures 212, 214, 216 to secure the ends with the connectors 204. The threaded fastener 220 may include a bore, such as a countersunk hexagonal bore, that receives a tool (not shown) for rotating the fastener 220 to thereby clamp the first ends 82, 84 between the caps 216 and the connectors 204.

When the outer most lobe on the first ends 82, 84 is positioned in the outer lobes of the connectors 204, the aperture 214 in the first ends 82, 84 is no longer aligned with the apertures 212 and 218. Instead, the first ends, 82, 84 include a cutout 222 that receives the threaded fastener when inserted through apertures 212 and 218. In any event, the caps 216 in conjunction with the lobed construction are sufficient to secure the ends 82, 84 to the connectors 204. As with the previous embodiments, stabilization system 180 may be incorporated within a larger spinal device. To this end, connectors 208 may be modified to include a channel 154 for insertion of a stabilization rod 148 as described above in reference to FIGS. 9 and 10.

Figure 11:
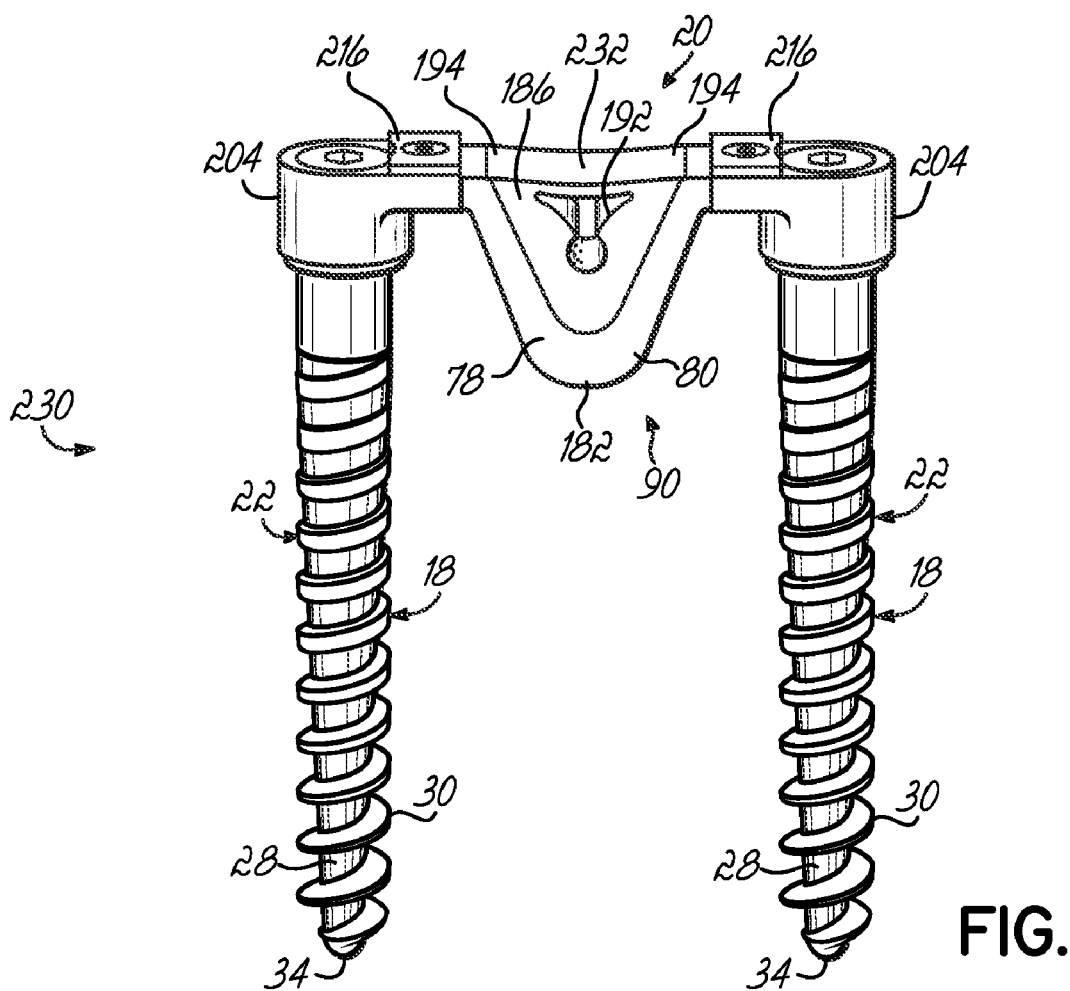
FIG. 11 is a perspective view of a stabilization system in accordance with an alternate embodiment of the invention.

FIG. 11, in which like reference numerals refer to like features in FIGS. 1-3 and FIGS. 9-10, illustrate a stabilization system 230 in accordance with another embodiment of the invention. The stabilization system 230 is similar to that shown in FIGS. 9 and 10 and only the differences will be discussed in detail. As noted above, the embodiment shown in FIGS. 9 and 10 is configured to prevent or reduce the likelihood of compressive overloading of the system 180 during, for example, extension of the spine 12. In that embodiment, however, there was no provision for preventing or reducing the likelihood of overloading the system 180 during tension.

For example, such tension may be imposed on the system 180 during flexion of the spine 12. The embodiment shown in FIG. 11 addresses tensile overloading of a stabilization system.

To this end, the cushion 186 includes a bridge member 232 spanning the cutout portion 192 along the upper surface 194. During compression, e.g., during extension of the spine 12, the bridge member 232 bends or buckles inwardly and imposes no biasing force that opposes movement of the spring arms 78, 80 toward each other. Accordingly, the cushion 186 would operate as that discussed above in regard to FIGS. 9 and 10. During tension, however, e.g., during flexion of the spine 12, the anchors 18, and therefore the spring arms 78, 80, move away from each other. In this case, the bridge member 232 stretches with such movement to generate a biasing force that opposes movement of the spring arms 78, 80 away from each other. The magnitude of the biasing force of the bridge member 232 typically increases with increased elongation of the bridge member 232. The amount of bias imposed by the bridge member 232 may be adjusted by, for example, varying the thickness of the bridge member 232. In this way, the bridge member 232 prevents or reduces the risk of damaging the stabilization system 230 due to tensile overloading.

Embodiments of the stabilization system as described herein and in accordance with the invention provide a number of advantages over current stabilization systems. For example, embodiments of the invention permit the distraction of the stabilization system to be adjusted in situ. In particular, the one-way adjustment feature afforded by the teeth 76, 96 on the tabs 72 of connectors 44 and ends 82, 84 of the spring arms 78, 80 permit the distraction to be quickly and conveniently adjusted. This adjustment may be performed without removing the stabilization system from the spine. The multi-lobed configuration shown in FIGS. 9 and 10 also permit adjustments to the distraction to be performed in situ.

Another advantage provided by embodiments of the stabilization system described herein is the movement of the rotational axis toward a more natural position. As noted above, current dynamic systems have a rotational axis at the posterior portion of the pedicle, while the normal rotational axis is at the posterior portion of the vertebral body. As illustrated in FIG. 1, the joint 90, which essentially provides the rotational axis of the stabilization systems in accordance with embodiments of the invention, has been moved in the anterior direction and toward the normal rotational axis of the spine. Thus, it is believed that the stabilization systems will give dynamic responses that more closely mimic the natural movements of the spine. Movement of the rotational axis in the anterior direction may also be beneficial for certain spinal diseases that affect the posterior portion of the spine. In effect, the rotational axis is now positioned in or toward a region of healthy tissue.

Yet another advantage of embodiments of the stabilization system of the invention is that the range of stiffness of the system has been increased and the ability to adjust the stiffness of the system has been improved. In particular, and as noted above, the length and thickness of the spring arms may be adjusted to provide the desired stiffness characteristic. Moreover, if a biasing member is being used, the stiffness of the biasing member may be manipulated to adjust the overall stiffness of the system. For example, the durometer of the spring ring 136 or cushion 186 may be varied to give a desired stiffness to the system. Moreover, the stiffness of the spring arms 78, 80 may be different depending on the specific application or disease being treated. Furthermore, spinal devices with stabilization systems on both the right and left sides of the spine may be configured such that the right and left stabilization systems have different stiffness characteristics.

While the present invention has been illustrated by a description of various preferred embodiments and while these embodiments have been described in some detail, it is not the intention of the inventors to restrict or in any way limit the scope of the appended claims to such detail. Additional advantages and modifications will readily appear to those skilled in the art. The various features of the invention may be used alone or in numerous combinations depending on the needs and preferences of the user.

What is claimed is:

1. A spinal stabilization apparatus, comprising:

first and second vertebral anchors, each of the first and second vertebral anchors having a head portion and a bone attachment portion extending from the head portion along a longitudinal axis to a tip of the bone attachment portion; and a flexible construct extending between the first and second vertebral anchors, the flexible construct including first and second spring arms forming a generally V-shape, the first spring arm having a first end coupled to the head portion of the first vertebral anchor and the second spring arm having a first end coupled to the head portion of the second vertebral anchor, a second end of the first spring arm being coupled to a second end of the second spring arm at a ball-and-socket joint, the first and second spring arms capable of flexing toward and away from each other during movement of the spine;

wherein the ball-and-socket joint allows relative rotational motion of the first spring arm relative to the second spring arm about an axis of rotation passing through the ball-and-socket joint that is generally perpendicular to the longitudinal axes of the first and second vertebral anchors and parallel to the spine; and wherein the axis of rotation of the ball-and-socket joint is positioned closer to the tips of the first and second vertebral anchors than the first ends of the first and second spring arms coupled to the head portions of the first and second vertebral anchors are.

2. The spinal stabilization apparatus of claim 1, wherein the flexible construct is formed of metal.

3. The spinal stabilization apparatus of claim 1, wherein the flexible construct is formed of PEEK.

4. The spinal stabilization apparatus of claim 1, further comprising a biasing member for opposing movement of the first and second spring arms relative to each other.

5. The spinal stabilization apparatus of claim 4, wherein the biasing member is a resilient spring ring.

6. The spinal stabilization apparatus of claim 4, wherein the biasing member is a resilient cushion.

7. The spinal stabilization apparatus of claim 4, wherein the biasing member is formed from polycarbonate urethane.

8. The spinal stabilization apparatus of claim 4, wherein the biasing member is configured to permit free movement of the first and second spring arms toward each other a specified amount before the biasing member imposes a biasing force opposing the motion.

9. The spinal stabilization apparatus of claim 8, wherein the biasing member includes a slot having spaced apart surfaces that engage each other after the specified amount of movement of the first and second spring arms.

10. The spinal stabilization apparatus of claim 9, further comprising a bridge member spanning the slot to oppose movement of the first and second spring arms away from each other.

11. The spinal stabilization apparatus of claim 4, wherein the biasing member only restricts movement of the first and second spring arms toward each other.

12. The spinal stabilization apparatus of claim 1, wherein the first end of at least one of the first and second spring arms includes a slot for coupling the first end with a respective vertebral anchor.

13. The spinal stabilization apparatus of claim 12, wherein the slot includes a plurality of teeth.

14. The spinal stabilization apparatus of claim 1, wherein the first end of at least one of the first and second spring arms has a multi-lobed configuration.

15. The spinal stabilization apparatus of claim 1, wherein the head portion of at least one of the first and second vertebral anchors includes a tab for coupling the head portion with the first end of the respective spring arm of the flexible construct.

16. The spinal stabilization apparatus of claim 15, wherein the tab includes a plurality of teeth.

17. The spinal stabilization apparatus of claim 15, wherein the tab includes a slot having a multi-lobed configuration.

18. The spinal stabilization apparatus of claim 1, wherein the head portion of at least one of the first and second vertebral anchors includes a first connecting member and the first end of at least one of the first and second spring arms includes a second connecting member, the first and second connecting members configured to provide a oneway adjustment feature.

19. The spinal stabilization apparatus of claim 1, wherein the first and second vertebral anchors are polyaxial screws.

20. The spinal stabilization apparatus of claim 1, wherein the head portion of at least one of the first and second vertebral anchors includes a connector for coupling the flexible construct to the first and second vertebral anchors through a snap-fit feature.

21. The spinal stabilization apparatus of claim 1, wherein the first spring arm has a stiffness characteristic which is different than a stiffness characteristic of the second spring arm.

22. The spinal stabilization apparatus of claim 21, wherein the stiffness characteristic of at least one of the first and second spring arms is adjusted by altering one of the length or thickness of the spring arm along an intermediate portion thereof.

23. The spinal stabilization apparatus of claim 1, wherein the stabilization apparatus is a portion of a larger spinal device.

24. The spinal stabilization apparatus of claim 23, wherein the spinal device includes dynamic stabilization portions and rigid stabilization portions.

25. The spinal stabilization apparatus of claim 1, wherein the flexible construct is configured to be coupled between the first and second vertebral anchors such that the ball-and-socket joint is positioned anterior of the head portions of the first and second vertebral anchors to more closely align with a natural center of rotation of the spine.

* * * * *